United States Patent [19]

Palmer et al.

[11] 4,342,699

[45] Aug. 3, 1982

[54] PROCESS FOR PRODUCTION OF MALEIC ANHYDRIDE

[75] Inventors: David A. Palmer; Juergen K. Holzhauer, both of Naperville, Ill.

[73] Assignee: Standard Oil Company (Indiana), Chicago, Ill.

[21] Appl. No.: 236,986

[22] Filed: Feb. 23, 1981

[51] Int. Cl.$^3$ ............................................. C07D 307/60
[52] U.S. Cl. ..................................................... 549/259
[58] Field of Search .................................... 260/346.75

[56] References Cited

U.S. PATENT DOCUMENTS

| | | | |
|---|---|---|---|
| 3,899,516 | 8/1975 | Dickason | 260/346.75 |
| 3,904,652 | 9/1975 | Frank | 260/346.75 |
| 3,919,257 | 11/1975 | Milberger et al. | 260/346.75 |
| 4,049,027 | 8/1977 | Anderson et al. | 260/346.75 |
| 4,062,872 | 12/1977 | Lew et al. | 260/346.4 |
| 4,152,339 | 5/1979 | Kerr | 260/346.75 |
| 4,203,906 | 5/1980 | Takada et al. | 260/346.4 |
| 4,222,945 | 9/1980 | Higgins et al. | 260/346.75 |
| 4,231,943 | 11/1980 | Paradis et al. | 260/346.75 |

FOREIGN PATENT DOCUMENTS

| | | |
|---|---|---|
| 2544972 | 4/1977 | Fed. Rep. of Germany . |
| 721412 | 1/1955 | United Kingdom . |
| 1030507 | 5/1966 | United Kingdom . |
| 1403395 | 8/1975 | United Kingdom . |

OTHER PUBLICATIONS

Calderbank and Caldwell, Chem. Reaction Engineering, Adv. in Chem. Series; 109 ACS, Wash., D.C., pp. 38–43, (1972).
Caldwell et al., British Chem. Engineering, 14(9), pp. 1199–1201, (1969).
Smith et al., Canadian J. of Chem. Engineering, 53, pp. 347–349, (1975).
Froment, Ind. and Engineering Chem., 59(2), pp. 18–27, (1967).
Sadhukhan et al., A. I. Ch. E. Journal, 22(4), pp. 808–810, (1976).
Calderbank et al., Proc. of the Fourth European Symp. on Chem. Reaction Engineering, Pergamon Press, Oxford, pp. 93–106, (1971).

*Primary Examiner*—John M. Ford
*Assistant Examiner*—Bernard Dentz
*Attorney, Agent, or Firm*—Stephen L. Hensley; William T. McClain; William H. Magidson

[57] ABSTRACT

Process for production of maleic anhydride comprising contacting n-butane-rich feed consisting essentially of n-butane, molecular oxygen and ballast gas with oxidation catalyst in a heat transfer medium-cooled, tubular reaction zone in which catalyst is graded in terms of reactivity such that reactivity increases to compensate for decreased reactant concentrations; removing effluent from the reaction zone; recovering maleic anhydride from the effluent; and recycling a major portion of the remaining effluent to the reaction zone.

22 Claims, 4 Drawing Figures

FLAMMABILITY DIAGRAM FOR n-BUTANE, OXYGEN AND NITROGEN

PROCESS FOR PRODUCTION OF MALEIC ANHYDRIDE

BACKGROUND OF THE INVENTION

This invention relates to the catalytic, vapor phase oxidation of n-butane to maleic anhydride. More particularly, the invention relates to an improved process for production of maleic anhydride wherein (1) a n-butane rich oxidation feed is oxidized to maleic anhydride in a heat transfer medium-cooled, tubular reaction zone, containing a fixed bed of catalyst graded in terms of reactivity, at relatively low per pass conversions of n-butane, (2) reactor effluent is withdrawn from the reaction zone and a major portion of maleic anhydride is separated therefrom, and (3) a major portion of the effluent remaining after separation is recycled to the reaction zone.

Catalytic, vapor phase oxidation of n-butane to maleic anhydride in heat transfer medium-cooled, tubular reaction zones is well known. Typically, a gaseous feed comprising molecular oxygen, n-butane and ballast gas is passed over a fixed bed of oxidation catalyst in one or more reaction tubes at temperatures of about 300° to about 650° C. and pressures of about 10 to about 75 psia. The oxidation reaction is highly exothermic and, in order to maintain the desired reaction zone temperature, heat transfer medium such as an oil or molten salt is circulated around the reaction tube or tubes. Typically, temperature of the heat transfer medium is adjusted to provide adequate cooling at the hottest point of the reaction zone. Effluent, typically comprising maleic anhydride, by-product oxygenated hydrocarbons, inert gases and unreacted n-butane and oxygen, is withdrawn from the reaction zone and maleic anhydride is substantially separated therefrom.

At present, known commercial processes for producing maleic anhydride from n-butane can be characterized as once through, air oxidation processes in that air is used as the source of molecular oxygen and, owing to the nitrogen content of air, levels of nitrogen in the reaction zone effluent build up to such an extent that recycle of effluent, with or without separation of nitrogen from unreacted n-butane, is economically impractical. In view of the flammability of mixtures of n-butane and air, concentrations of n-butane in a once through, air oxidation feed typically are limited to about 1.8 mole%, and even this is slightly within the flammable region. As a result of such limitations on feed n-butane, the amount of maleic anhydride that can be produced per unit of reaction zone capacity is limited. Further, due to the impracticality of recycling unreacted n-butane, the same typically is discarded such that the amount of maleic anhydride produced per amount of n-butane consumed is lower than would be desirable.

In an attempt to improve productivity and n-butane consumption, it has been proposed to employ oxidation feeds containing higher concentrations of n-butane than typically are used in the above-described once through, air oxidation processes and/or to recycle reaction zone effluent. For example, U.S. Pat. No. 3,899,516 (Dickason) discloses that space time yields and catalyst selectivity to maleic anhydride can be improved through the use of a feed containing n-butane and substantially pure (at least 95%) molecular oxygen in a molar ratio of at least 1:4, i.e., at least 20 mole% n-butane and less than 80 mole% oxygen in the feed. Commonly assigned U.S. Pat. No. 3,904,652 (Frank) discloses the use of feeds containing greater than 1.7 mole% n-butane, 3–13 mole% oxygen, and 70–95 mole% inert gas, preferably nitrogen, in conjunction with 30 to 70% per pass conversions of n-butane and recycle of reactor effluent after separation of maleic anhydride in order to attain improved selectivity to maleic anhydride and ultimate conversions of n-butane. Similarly, U.S. Pat. No. 4,044,027 (Anderson et al.), which is directed primarily to improving product quality and yield by rapid cooling of reactor effluent so as to avoid decomposition of maleic anhydride and formation of color bodies, discloses the use of feeds containing at least 1.5 mole% n-butane and less than 20 mole% oxygen in conjunction with less than 50% per pass conversion and recycle of a portion of the reactor effluent after separation of maleic anhydride and at least some unreacted n-butane therefrom. W. German Offen. No. 2,544,972 (Hoechst) discloses a process for producing maleic anhydride from mixed butane isomers wherein a butane and air feed is oxidized, followed by removal of effluent from the reaction zone, separation of maleic anhydride from the effluent, recycle of 75 to 98% of the effluent remaining after separation to the reaction zone with addition of make-up air and butanes, adsorption of butanes from the remaining 2 to 25% of the effluent on active carbon, desorption of butanes with fresh air and charging of the butane-laden air to the reaction zone.

Despite the improvements reported in the above-described patents, the same are not entirely satisfactory from the standpoint of operation of the heat transfer medium-cooled reaction zone. As noted hereinabove, temperature of the heat transfer medium is determined on the basis of the temperature at the hottest point of the reaction zone. That point, also referred to as "hot spot," is located at the point at which the oxidation rate is maximum and the reaction is most exothermic. Given the positive dependency of reaction rates on reactant concentrations, reaction zone hot spot typically is located near the feed end of the zone because that is where reactant concentrations are highest. In the above-described butane-rich processes, feed end reaction rates are even greater than in typical air oxidation processes due to increased n-butane concentrations. Above a certain concentration of n-butane, heat of reaction cannot be removed due to poor heat transfer in the reaction zone. As a result, catalyst damage and/or thermal runaway of the oxidation reaction can occur. Even if the n-butane concentration is not so high as to cause a thermal runaway, attempts to remove heat of reaction from the reaction zone feed end by adjustment of heat transfer medium temperatures can lead to problems downstream from the feed end. Thus, reactants are consumed as they progress from the feed end of the reaction zone to the exit end with the result that reactant concentrations, and accordingly reaction rates and the amount of heat liberated, decrease. While the heat transfer medium provides adequate cooling in the vicinity of the reaction zone hot spot, the decreased amounts of heat liberated downstream from the feed end typically are insufficient to compensate for the degree of cooling provided near the feed end. Thus, downstream from the feed end of the reaction zone, reaction rates are limited not only by decreased reactant concentrations, but also by excessive cooling. As a result, productivity suffers.

It has been proposed to improve temperature control and operation in various processes involving exothermic reactions by employing a reaction zone in which catalyst activity varies along the length of the zone and such proposals may be of interest with respect to the present invention. Thus, British Pat. No. 721,412 (Chem Patents) discloses oxidation of olefins, and particularly ethylene, in reaction tubes immersed in cooling medium and packed with supported silver catalyst in such a manner that activity increases from the inlet to the outlet of the tubes. Dilution of effluent remaining after removal of product followed by recycle of the diluted effluent also is disclosed. According to the patentee, the use of a graded catalyst results in increased productivity and allows for sustained operation without hot spot formation; however, there is no suggestion that grading of the catalyst bed can be employed to allow for operation on the hydrocarbon rich side of the flammability zone, nor is it disclosed to employ graded catalyst as a means for improving productivity. Further, results in the silver-catalyzed oxidation of ethylene cannot be readily translated to processes for oxidation of n-butane to maleic anhydride.

G. F. Froment, *Industrial and Engineering Chemistry*, 59 (2), pp. 18–27 (1967) proposes a two-dimensional model for hydrocarbon oxidations in fixed bed, tubular reactors and suggests that hot spot can be eliminated and average reaction zone temperature can be increased by appropriate dilution of catalyst with inert packing in the early stages the catalyst bed.

Caldwell and Calderbank, *British Chemical Engineering*, 14 (9) pp. 1199–1201 (1969) discuss the aforesaid problems of temperature control in tubular reactors and propose dilution of catalyst in the vicinity of the reaction zone hot spot as a means for attaining increased conversions without making the reaction zone more sensitive to variations in operating conditions. The authors also postulate an equation for calculating the catalyst dilution, as a function of temperature and conversion, required to achieve desired temperature gradients.

Calderbank, Caldwell and Ross, "*Proceedings of the Fourth European Symposium on Chemical Reaction Engineering,*" Pergamon Press, Oxford, pp 93–106 (1971) present one- and three-dimensional models of exothermic catalytic reactions carried out in fixed-bed reactors containing graded catalyst.

Calderbank and Caldwell, *Chemical Reaction Engineering, Advances in Chemistry Series*, 109 ACS, Washington, D.C., pp 38–43 (1972) discuss oxidation of o-xylene to phthalic anhydride in tubular reactors containing graded catalyst.

Smith and Carberry, *The Canadian Journal of Chemical Engineering*, 53, pp. 347–349 (1975), although silent with respect to grading of catalysts, disclose the use of partially impregnated catalysts, primarily in conjunction with the oxidation of naphthalene to phthalic anhydride, and conclude that improved yields, higher average reaction zone temperatures and decreased catalyst consumption can result.

Despite the teachings of the aforesaid British patent and the theory and mathematical relationships presented in the literature references, the same do not disclose or suggest the use of a graded catalyst bed to permit smooth operation on the hydrocarbon rich side of the flammability zone nor as a means for permitting economically practical recycle in the production of maleic anhydride from n-butane. The references also fail to disclose actual reactivity gradients useful in oxidation of a given feed to a given product under given conditions. Further, the specific processes addressed by the references, e.g. oxidation of ethylene to ethylene oxide, o-xylene to phthalic anhydride and naphthalene to phthalic anhydride, are sufficiently different from oxidation of n-butane to maleic anhydride as to preclude direct application of the references' teachings and theory to n-butane oxidation. Thus, for example, for a given volume of gas, operation at hydrocarbon concentrations at the lower explosive limits results in evolution of twice as much heat in the case of n-butane oxidation as in the case of oxidation of o-xylene to phthalic anhydride. Accordingly, heat removal requirements in the former are more severe.

From the foregoing, it can be appreciated that it would be desirable to provide a process for production of maleic anhydride wherein the advantages of a n-butane-rich oxidation feed can be better exploited. It is an object of this invention to provide such a process. A further object of the invention is to provide for increased productivity per unit of reaction zone capacity in the production of maleic anhydride from n-butane. A further object of the invention is to provide for improved utilization of n-butane. Another object of the invention is to provide a process wherein recycle of reaction zone effluent is made economically practical. A still further object of the invention is to provide a process that can be operated safely on the hydrocarbon-rich side of the flammability envelope. A further object is to provide a process that can be implemented in conventional once through air oxidation facilities without loss of substantial capacity. Other objects of the invention will be apparent to persons skilled in the art from the following description and the appended claims.

We have now found that the objects of this invention can be attained by contacting a n-butane rich oxidation feed with oxidation catalyst at relatively low per pass conversions of n-butane in a heat transfer-medium-cooled tubular reaction zone in which the catalyst is graded in terms of reactivity, with recycle of a major portion of maleic anhydride-free reaction zone effluent to the reaction zone. Advantageously, the use of a n-butane rich feed in conjunction with graded catalyst results in improved productivity of maleic anhydride as compared to typical air oxidation processes and n-butane rich processes using ungraded catalyst. Further, grading of the catalyst bed results in a more uniform temperature profile over the effective length of the reaction zone such that reaction zone capacity is better utilized. In addition, operation at relatively low per pass conversions can give improved selectivities to maleic anhydride, and this in combination with recycle of unreacted n-butane can result in improved yields of maleic anhydride. Ultimate conversions of n-butane also are improved. As compared to conventional, once through air oxidation processes, operation according to this invention can give up to twice the throughput for a given reaction zone capacity, with decreased catalyst consumption due to grading of the catalyst bed.

DESCRIPTION OF THE INVENTION

Briefly, the present invention provides a process for producing maleic anhydride which comprises (A) contacting a feed consisting essentially of about 2 to about 10 mole% n-butane, about 8 to about 20 mole% molecular oxygen and a balance of inert gas or gases with oxidation catalyst in a heat transfer medium-cooled, tubular reaction zone maintained under oxidation conditions effective to provide a relatively low per pass conversion of n-butane, said catalyst being graded along at least a portion of the effective length of the reaction zone from minimum reactivity nearest a feed end of the reaction zone to maximum reactivity nearest an exit end of the reaction zone; (B) withdrawing from the exit end of the reaction zone an effluent comprising maleic anhydride, by-product oxygenated hydrocarbons, inert gases, and unreacted oxygen and n-butane; (C) separating a major portion of maleic anhydride and by-product oxygenated hydrocarbons from the reaction zone effluent; (D) removing from the effluent remaining after recovery of maleic anhydride and oxygenated hydrocarbon by-products a purge stream at a rate substantially corresponding to the rate of build-up of inert gases in the reaction zone; and (E) recycling effluent remaining after removal of the purge stream to the reaction zone with addition of make-up gas comprising n-butane and molecular oxygen.

In greater detail, a typical heat transfer medium-cooled, tubular reaction zone employed according to this invention comprises one or more hollow tubes, preferably with length to diameter ratios ranging from about 25 to about 500, such tubes being encased within a shell containing circulating heat transfer medium. The tubes preferably are constructed of carbon steel or stainless steel although other materials having a high degree of mechanical strength, corrosion resistance and chemical inertness also are suitable. The shell that encases the tube or tubes can be constructed from any suitable material but preferably is made of a carbon steel. The shell is provided with heating means, for example, an external electric coil or heater, to heat the heat transfer medium to the desired startup temperature. Cooling means, such as a steam boiler, also are provided to maintain the heat transfer medium at the desired temperature during oxidation. Circulation of heat transfer medium around the tube or tubes is conveniently accomplished through the use of a stirrer, a pump and baffle arrangement, or other suitable means.

Heat transfer media useful according to this invention are well known to persons skilled in the art and, in general, are materials that remain in the liquid state at process temperatures and have a relatively high thermal conductivity. Examples of useful media include various heat transfer oils, and salts such as nitrates and nitrites of alkali metals, the salts being preferred due to their higher boiling points. A particularly preferred heat transfer medium is a eutectic mixture of potassium nitrate, sodium nitrate and sodium nitrite which not only has a desirably high boiling point, but also, a sufficiently low freezing point that it remains in the liquid state even during periods of reaction zone shutdown.

Catalyst is loaded into the reaction tube or tubes in such a manner that reactivity increases over at least a portion of the effective reaction zone length from minimum reactivity nearest the feed end of the reaction zone to maximum reactivity nearest the exit end. For purposes hereof, effective reaction zone length is defined as the catalyst-containing portion of the reaction zone. Preferably, effective length is at least about 75% of overall length, with any remaining length forming one or two substantially dead, e.g., catalyst free, zones at the feed and/or exit ends of the reaction zone. More preferably, effective reaction zone length makes up about 80 to about 100% of overall length. As between feed end and exit end dead zones, the former is preferred because it can serve as a preheating zone for the oxidation feed introduced into the reaction zone.

Preferably, the entire effective length of the reaction zone is graded from minimum reactivity nearest the feed end to maximum reactivity nearest the exit end. However, it also is contemplated to grade only a portion of the effective length of the reaction zone from minimum reactivity nearest the feed end to maximum reactivity nearest the exit end. For example, proceeding from the feed end of the reaction zone to the exit end, a first portion of the effective reaction zone length can have high or intermediate reactivity and the remainder of the effective length can be graded from minimum to maximum reactivity. The initial high or intermediate reactivity zone preferably is relatively short and can give beneficial results in that the same can serve as a preheating zone for the oxidation feed. Such a reactivity gradient is illustrated in FIG. 4 and further described hereinbelow. It also is contemplated to grade the effective length from minimum to maximum reactivity over a first segment and provide an intermediate or low reactivity zone at the exit end of the reaction zone although this is not a preferred embodiment because the benefits associated with providing maximum reactivity at the area of minimum reactant concentration are reduced. These configurations also can be combined such that only a central portion of the effective length is graded from minimum reactivity nearest the feed end to maximum reactivity nearest the exit end. In that case, reactivity decreases from the segment of the effective length nearest the reaction zone feed end to the minimum reactivity portion of the central portion, increases across the central portion, and decreases from the maximum reactivity portion of the central portion to the lower reactivity portion nearest the exit end.

That portion of the effective reaction zone length that is graded from minimum reactivity nearest the feed end to maximum reactivity nearest the exit end can be graded continuously and/or in stages. Ideally, reactivity increases continuously from minimum to maximum reactivity; however, from a practical standpoint, it is more convenient to provide two or more reactivity zones or stages along the portion of the effective reaction zone length to be graded from minimum to maximum reactivity. Preferably, the number of zones ranges from two to about 20, with about three to about eight being more preferred from the standpoint of attaining a relatively uniform temperature profile, and accordingly, high productivity, without incurring excessively high catalyst loading costs.

For a given process, precise location, length and relative reactivities of the various zones will vary depending on a variety of factors such as overall and effective reaction zone lengths, production rate, choice of catalyst and reaction conditions, and can be determined by experimentation in accordance with the examples appearing hereinbelow. Preferably, the minimum reactivity zone nearest the feed end extends over about 10 to about 50% of the effective reaction zone length and reactivity ranges from about 10 to about 75% of that in the maximum reactivity zone nearest the exit end, with the remainder of the effective length containing one or more zones of increasing reactivity. For purposes hereof, reactivity can be expressed on a relative basis with a 100% value being assigned to the maximum reactivity segment of that portion of the effective reaction zone length graded from minimum reactivity nearest the feed end to maximum reactivity nearest the exit end. Correspondingly higher or lower values can be assigned to other segments based upon the rate of n-butane conversion therein relative to the rate in the 100% zone.

Any suitable means for providing the desired reactivity gradient is contemplated according to this invention. Most simply, pelleted oxidation catalyst is employed, with the desired gradation being accomplished by blending of catalyst pellets with an inert solid. Suitable inert solid diluents include materials which do not adversely affect catalyst performance in the oxidation reaction and which are at least roughly similar to the catalyst pellets in terms of size and shape, so that a substantially uniform flow of gas through the catalyst bed is ensured. Specific examples of useful solid diluents include silica, alumina and carborundum pellets. A continuous reactivity gradient can be provided by feeding catalyst pellets and inerts to the reaction tube or tubes using serparate variable speed feeders. Staged gradient can be provided by batchwise blending of catalyst pellets and inerts in appropriate amounts.

A related method of achieving the desired reactivity gradient is to employ a supported catalyst in which the proportion of support decreases, and correspondingly, the proportion of active catalyst increases, from the minimum to maximum reactivity zones. Partial impregnation of support with catalyst can give particularly good results in that selectivity typically is improved. Suitable supports are described in detail hereinbelow.

A third method for grading the catalyst bed involves the use of different catalysts in the individual reactivity zones, with catalyst of maximum reactivity being employed in the maximum reactivity zone nearest the exit end, catalyst of lowest reactivity being employed in the minimum reactivity zone nearest the feed end, and one or more catalysts of intermediate reactivity being used in any intermediate reactivity zone or zones. Particularly good results are attained when the lower reactivity catalysts have high selectivities.

Another method for achieving the desired gradient is to use blends of catalysts of varying reactivities containing varying proportions of the individual catalysts in the different reactivity zones.

Of course, various combinations of the above or other techniques also can be employed to attain a reactivity gradient tailored to specific process equipment or requirements.

Oxidation catalysts useful according to this invention are known to the art, and, in general, are materials capable of catalyzing the oxidation of n-butane to maleic anhydride under oxidation conditions. Examples of useful catalysts are discussed hereinbelow, it being understood that the same are for purposes of illustration and guidance in the practice of the invention.

One class of catalysts useful according to the invention is the phosphorus-vanadium-oxygen complex catalysts. Such catalysts typically contain about 0.5 to about 5 atoms of phosphorus per atom of vanadium and are prepared by reaction of compounds of phosphorus and vanadium in aqueous or organic medium followed by heating of the resulting solid. Suitable phosphorus compounds include phosphorus pentoxide, phosphoric acid, orthophosphorus acid, phosphorus trichloride, phosphorus trioxide and triethyl phosphate, and suitable vanadium compounds include vanadium oxalate, vanadium formate, ammonium metavanadate, vanadyl trichloride, metavanadic acid, vanadium sulfate and vanadium phosphate. Reaction of such compounds is conducted in an aqueous or organic medium to form a solid reaction product which is isolated by evaporation of supernatant liquid. Subsequently, the solid is activated by heating at about 300° to about 600° C. and ground and/or pelleted. Activation can be conducted before or after grinding and/or pelleting. Optionally, the catalyst is blended with a suitable inert support, for example alpha alumina or silicon carbide, prior to use. Further details with respect to such phosphorus-vanadium-oxygen complex catalysts are found in U.S. Pat. Nos. 3,293,268 (Bergman et al.) and 3,907,707 (Raffelson et al.) which are incorporated herein by reference.

Phosphorus-vanadium-oxygen complex catalysts also can be prepared by fusion of phosphorus pentoxide into a vanadium pentoxide matrix as disclosed in U.S. Pat. No. 3,907,833 (Slinkard et al.).

A second class of useful catalysts is the metal-promoted phosphorus-vanadium-oxygen complexes. Such catalysts typically contain about 0.5 to about 5 atoms of phosphorus per vanadium atom and, in addition, from about 0.001 to about 5 atoms of at least one metal promoter per vanadium atom. Useful promoters include the alkali and alkaline earth metals, scandium, lanthanum, yttrium, cesium, neodymium, samarium, titanium, zirconium, hafnium, niobium, tantalum, chromium, tungsten, molybdenum, manganese, rhenium, iron, cobalt, nickel, palladium, copper, silver, zinc, cadmium, aluminum, gallium, indium, silicon, germanium, tin, antimony, bismuth, tellurium, thorium and uranium. In general, one or more of these promoters is incorporated into a phosphorus-vanadium-oxygen complex before, during or after the complex-forming reaction. Such catalysts can be either supported or unsupported. Further details with respect to such catalysts are found in the following patents which are incorporated herein by reference:

U.S. Pat. Nos. 3,862,146 (PVO promoted with Zr, Bi, Cu, Li);

3,832,359 (PVOFe complex);

3,905,914; 3,931,046 and 3,932,305 (PVOZr complexes);

U.S. Pat. No. 3,980,585 (PVO promoted with Te, Zr, Ni, Ce, W, Pd, Ag, Mn, Cr, Zn, Mo, Re, Sm, La, Hf, Ta, Th, Co, U, or Sn, and in addition an alkali or alkaline earth metal);

U.S. Pat. Nos. 4,062,873 and 4,064,070 (PVOSi complex);

U.S. Pat. No. 4,147,661 (PVO promoted with W, Sb, Nb, and/or Mo);

U.S. Pat. No. 4,151,116 (PVO promoted with "post-deposited" Mg, Ca, Se, Y, La, U, Ce, Cr, Mn, Fe, Co, Ni, Cu, Zn, Al, Ga, In, Si, Ge, Sn, Bi, Sb, or Te; optionally, Ti, Zn, Hf, Li, Mg, Ca, Fe, Co, Ni, Cu, Sn, Bi, U, a rare earth metal, Cr, Cd or Al is incorporated into the complex prior to post-deposition of promoter);

U.S. Pat. No. 4,152,338 (PVO promoted with Nb, Cu, Mo, Ni, Co and Cr, preferably containing, in addition, Ce, Nd, Ba, Hf, U, Ru, Re, Li or Mg);

U.S. Pat. No. 4,152,339 (PVOCu promoted with Te, Zr, Ni, Ce, W, Pd, Ag, Mn, Cr, Zn, Mo, Re, Sm, La, Hf, Ta, Th, Co, U or Sn, preferably also containing an alkali or alkaline earth metal);

U.S. Pat. Nos. 4,153,577 and 4,158,671 (PVO promoted with Cu, Mo, Ni, Co, Cr, Nd, Ce, Ba, Y or Sm);

1,403,395 (PVOTi optionally containing $WO_3$ and/or $MoO_3$).

A third group of catalysts is that wherein the primary metal is other than vanadium. For example, U.S. Pat. No. 2,691,660 discloses butane oxidation catalysts comprising molybdenum, and cobalt or nickel oxides, and optionally, a promoter selected from boron, phosphorus and vanadium oxides, silicon, tungsten, titanium beryllium, zirconium, chromium and uranium. U.S. Pat. No. 3,928,392 discloses butane oxidation catalysts comprising oxides of antimony, molybdenum, and nickel, cobalt, copper or zinc. U.S. Pat. No. 4,065,468 discloses butane oxidation catalysts comprising the combined oxides of antimony, molybdenum, and vanadium or iron, optionally containing, in addition, one or more oxides of aluminum, boron, tellurium, chromium cobalt, nickel, copper, bismuth, phosphorus, titanium or tungsten.

The presently preferred catalysts for use according to this invention are the metal-promoted phosphorus-vanadium-oxygen complex catalysts such as those according to U.S. Pat. No. 3,862,146.

Oxidation according to this invention is carried out in the above-described heat transfer medium-cooled, tubular reaction zone containing graded catalyst by introducing a feed consisting essentially of about 2 to about 10 mole% n-butane, about 8 to about 20 mole% molecular oxygen and a balance of inert gas or gases into the feed end of the reaction zone maintained under conditions such that a relatively low per pass conversion of n-butane is attained. An effluent, comprising maleic anhydride, by-product oxygenated hydrocarbons, unreacted n-butane and oxygen, and inert gas or gases, is withdrawn from the exit end of the reaction zone and maleic anhydride and oxygenated hydrocarbon by-products are substantially separated therefrom after which the remaining effluent is separated into a purge stream, that is removed at a rate that substantially compensates for the build-up of inerts in the reaction zone, and a recycle stream that is recycled to the reaction zone with addition of make-up gas comprising n-butane and molecular oxygen.

The composition of the oxidation feed employed according to this invention is important not only from the standpoint of attaining desirable yields of maleic anhydride, but also with respect to safe reaction zone operation. As indicated hereinabove, the feed preferably contains levels of n-butane on the hydrocarbon-rich side of the flammability envelope. Irrespective of n-butane concentration, feed gas concentrations should be adjusted to avoid formation of flammable mixtures. Generally, at n-butane concentrations in the upper portion of the aforesaid range, oxygen concentrations in the higher portion of the aforesaid range are employed. Conversely, at lower n-butane concentrations, lower oxygen levels should be employed.

Further detail with respect to feed composition is provided in FIG. 1 of the drawing which illustrates the flammability envelope for mixtures of molecular oxygen, n-butane and a balance of nitrogen at room temperature at atmospheric pressure. Point 1 is illustraive of feed compositions in typical once through air oxidations, while points 2–4 illustrate feed compositions employed according to this invention. Points 3 and 4 illustrate feeds containing preferred levels of n-butane and oxygen in that the same are on the n-butane rich side of the flammability zone, and accordingly, result in improved productivity. It should be recognized that the FIG. 1 flammability curve is specific to gaseous mixtures in which the inert gas is nitrogen. When carbon dioxide is present in the inert gases, such as in the preferred embodiments of this invention, the flammable region decreases somewhat. Elevated temperatures and pressures expand the flammable region.

The n-butane used according to this invention preferably is substantially pure, i.e., at least about 96%. However, it also is contemplated to include up to about 20 mole% of one or more other oxidizable $C_4$ hydrocarbons such as isobutane, butenes or butadienes in the feed.

The molecular oxygen source used according to the invention has a substantial effect on productivity. Substantially, i.e., at least 95%, pure oxygen is preferred because the amount of ballast gas required to avoid formation of a flammable mixture in the reaction zone is supplied in whole by the recycle stream in which case the purge stream removed from the reaction zone effluent prior to recycle need only be great enough to compensate for the levels of carbon oxides produced during oxidation. On the other hand, if oxygen of lower purity is used, a larger purge stream is required in order to compensate not only for formation of carbon oxides as a result of the oxidation but also for the inerts introduced with the molecular oxygen.

The ballast gas supplied to the reaction zone will vary depending on the molecular oxygen source. If substantially pure oxygen is used the ballast gas provided by the recycle stream is predominantly a mixture of carbon monoxide and carbon dioxide. The molar ratio of carbon monoxide to carbon dioxide is a function of catalyst choice, but generally ranges from about 0.5:1 to about 2.5:1. In addition to minimizing purge stream requirements, the use of substantially pure oxygen and attendant presence of carbon dioxide in the ballast gas facilitates temperature control due to the high heat capacity of carbon dioxide. If the molecular oxygen source to be used is air, the ballast gas, of course, will contain substantial amounts of nitrogen. Similarly, if a mixture of molecular oxygen and one or more inert gases constitutes the molecular oxygen source, the ballast gas will include the inert gas or gases introduced with the oxygen. If ballast gas other than that provided in the recycle stream and/or that introduced to the reaction zone with the oxygen must be introduced to the reaction zone to adjust the feed composition, it is preferred to use nitrogen, carbon monoxide, carbon dioxide or mixtures thereof. Mixtures of carbon monoxide with carbon dioxide containing enough of the latter to reduce the flammability zone are more preferred.

Preferably, the oxidation feed contains from about 3 to about 8 mole% n-butane, about 10 to about 18 mole% molecular oxygen and about 74 to about 87 mole% ballast gas. When substantially pure oxygen is used as the molecular oxygen source, ballast gas preferably comprises about 30 to about 50 mole% carbon monoxide, about 35 to about 55 mole% carbon dioxide and less than about 1 mole% nitrogen. If air is the molecular oxygen source, ballast gas preferably comprises about 70 to about 85 mole% nitrogen, up to about 5 mole% carbon dioxide and about 1 to about 10 mole% carbon monoxide. For a feed containing 5.5 mole% n-butane, 14 mole% oxygen and a balance of carbon monoxide and carbon dioxide in a molar ratio of about 1.1:1, a safety margin of 1.2 mole% n-butane or 1.6 mole% oxygen exists with respect to the flammability limit.

The oxidation feed is introduced into the feed end of the reaction zone which is maintained under reaction conditions effective to attain relatively low per pass conversions of n-butane. For purposes hereof, per pass conversion is defined as 100% times the number of moles of n-butane oxidized divided by the number of moles of n-butane in the feed. Preferably, the per pass conversion rate ranges from about 15 to about 70%, and more preferably, from about 30 to about 55% in order to attain high ultimate conversions with good selectivity to maleic anhydride. Reaction conditions include temperature, pressure, space velocity, and others as discussed in greater detail hereinbelow.

Reaction zone temperature is sufficiently high to attain reasonable reaction rates but not so high as to damage the oxidation catalyst or promote undesirable side reactions. Preferred temperatures range from about 300° to about 650° C., with about 350° to about 500° C. being more preferred. It is desirable to preheat the oxidation feed to within about 100° C. of reaction temperature prior to passing the feed over that portion of the catalyst bed that is graded from minimum to maximum reactivity.

Reaction zone pressure is not critical although from a practical standpoint it is preferred to operate at about 10 to about 70 psia.

The oxidation feed is fed to the reaction zone at a rate such that relatively low per pass n-butane conversions are attained. Preferably, volumetric space velocity of the feed ranges from about 1000 to about 3000/hour. More preferably, volumetric space velocity ranges from about 1500 to about 2500/hour as the same result in desirable productivity without excessive pressure drop from the feed end to the exit end of the reaction zone. At volumetric space velocities of about 1500 to about 2500/hour, per pass n-butane conversions typically range from about 30 to about 50%. Contact time in the reaction zone varies depending on space velocity and pressure and typically ranges from about 0.5 to about 4 seconds.

From the exit end of the reaction zone there is withdrawn an effluent comprising maleic anhydride, by-product oxygenated hydrocarbons, inert gas or gases and unreacted n-butane and oxygen. Primary by-product oxygenated hydrocarbons include acetic and acrylic acids which typically are produced in amounts somewhat greater than in conventional once through air oxidations. The effluent is passed to a separation zone in which maleic anhydride and by-product oxygenated hydrocarbons are substantially recovered. The remaining effluent is divided into purge and recycle streams and the latter is returned to the reaction zone together with make-up gas comprising oxygen and n-butane.

Separation of maleic anhydride and by-product oxygenated hydrocarbons from the reaction zone effluent can be accomplished by any suitable means. For example, the effluent can be scrubbed with an aqueous liquid, e.g., an aqueous solution of maleic acid, and the resulting scrubber solution dehydrated to convert maleic acid to the anhydride. Acetic and acrylic acids, also removed from the effluent by scrubbing, pass overhead during dehydration and can be recovered by fractionation, extraction or other suitable means.

Another method for recovering maleic anhydride from the effluent is to condense a portion of the anhydride out of the effluent prior to scrubbing of effluent and dehydration of maleic acid. Partial condensation prior to scrubbing can give beneficial results in terms of maleic anhydride yields in that less of the anhydride is converted to acid, and accordingly, less acid is available for irreversible isomerization to fumaric acid. Further, reduced levels of maleic and fumaric acids are advantageous because the acids are solids under recovery conditions and can plug processing equipment.

Another suitable method for recovery of maleic anhydride and by-product oxygenated hydrocarbons is to contact the effluent with an organic solvent having low absorption capacity for water and high absorption capacity for maleic anhydride, and then strip the maleic anhydride from the solvent. In this manner, hydrolysis of maleic anhydride to the acid is substantially avoided thus resulting in improved yields of maleic anhydride. Useful absorbants include a variety of organic solvents, specific examples of which are found in U.S. Pat. No. 3,891,680 (Katsumoto et al.) and 4,118,403 (White).

Effluent remaining after substantial recovery of maleic anhydride and by-product oxygenated hydrocarbons, comprising inert gases and unreacted n-butane and oxygen, is divided into a purge stream and a recycle stream. The purge stream is removed at a rate that substantially compensates for the build up of inerts in the reaction zone. The precise rate of removal depends upon a variety of factors such as source of molecular oxygen, production rate, reaction zone capacity, choice of catalyst and oxidation conditions as can be appreciated by persons skilled in the art. When substantially pure oxygen is used as the source of molecular oxygen, preferred purge rates range from about 1 to about 20 mole% of the effluent gas. If air is the molecular oxygen source, purge rates of about 20 to about 75 mole% are preferred.

After removal of the purge stream, the remaining effluent is recycled to the reaction zone. As noted hereinabove, if substantially pure oxygen is used as the molecular oxygen source, only n-butane and oxygen need be supplied to the reaction zone as make-up gases because the recycle stream will provide adequate levels of inert gases for the oxidation feed. If air or low purity oxygen is the molecular oxygen source, inert gas or gases will accompany the make-up oxygen.

A preferred manner of operating in accordance with the present invention is described in greater detail in conjunction with the drawing wherein.

Figure 1:
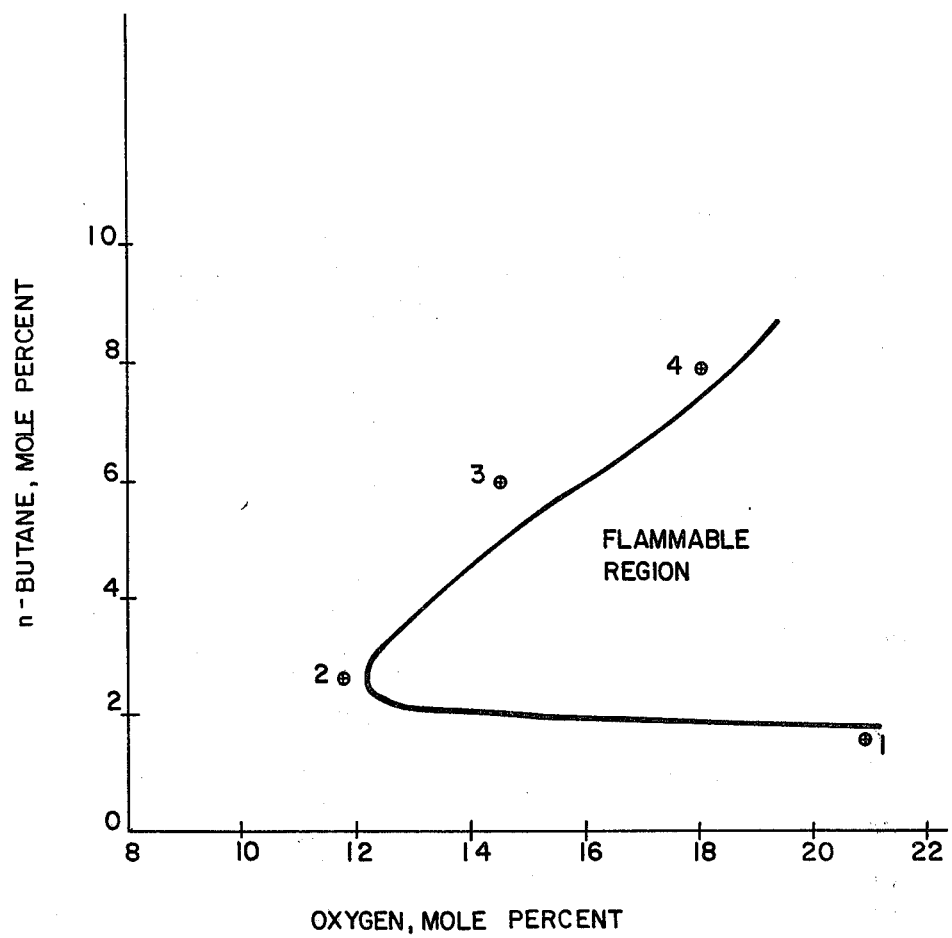
Figure 2:
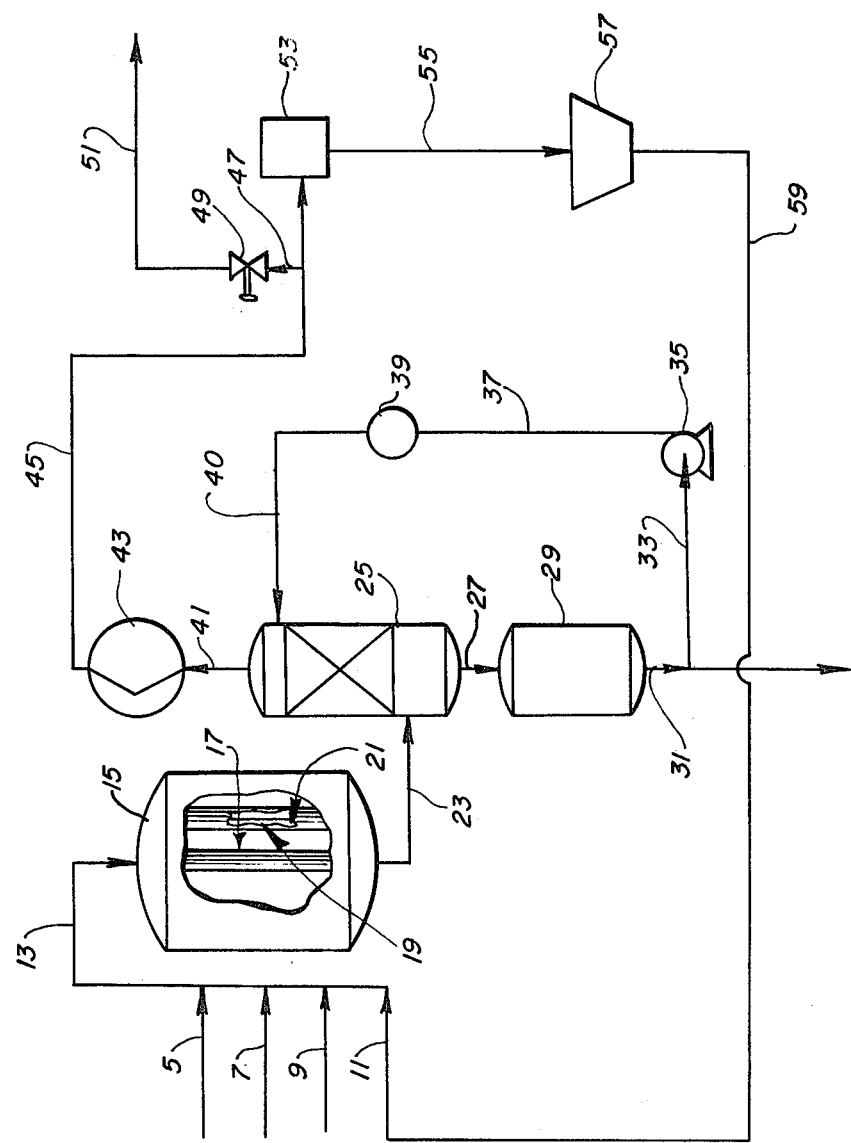
FIG. 2 illustrates a process diagram.

Referring to FIG. 2, on startup n-butane and air are metered from n-butane and air sources (not shown) to feed line 13 via lines 5 and 7 respectively. The feed is introduced into the feed end of reactor 15 which is shown with a portion of its wall cut away to reveal reaction tubes 17 and 19. The reactor also contains circulating molten salt (not shown). A portion of the wall of tube 19 is cut away to reveal centrally extending thermowell 21 which is used for temperature measurement. Tubes 17 and 19 are loaded with catalyst (not shown) graded in terms of reactivity.

Figure 3:
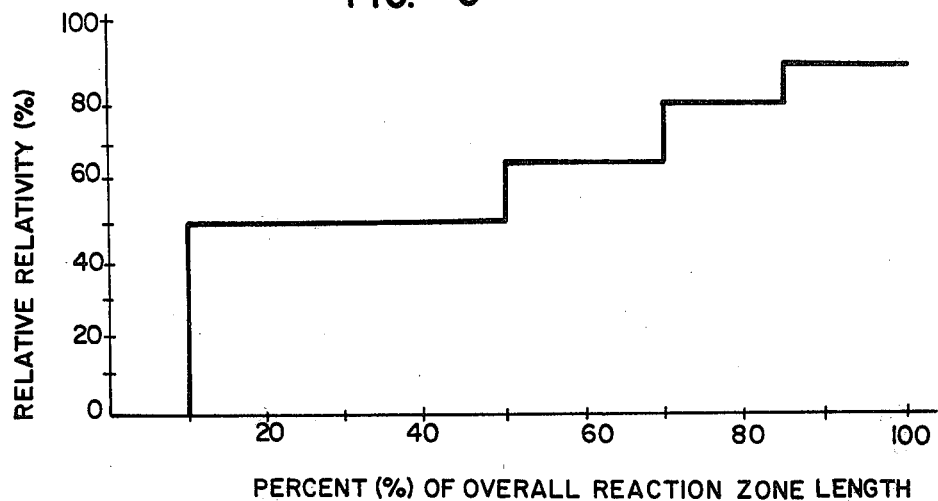
FIGS. 3 and 4 illustrate preferred catalyst gradient profiles.
Figure 4:
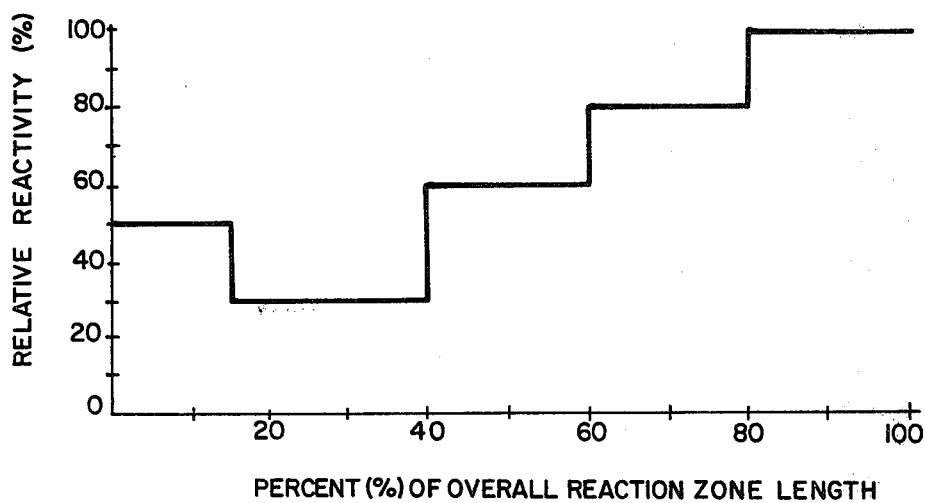

Preferred reactivity gradient profiles are shown in FIGS. 3 and 4 wherein reaction zone length is plotted on the abscissa—with 0% corresponding to the feed end and 100% corresponding to the exit end—and relative reactivity is plotted on the ordinate. According to the FIG. 3 profile, the entire effective length of the reaction zone is graded from minimum reactivity nearest the feed end to maximum reactivity nearest the exit end. A dead zone, with 0% reactivity, makes up the first 10% of the overall reaction zone length and serves as a preheating zone for the oxidation feed. The reactivity profile illustrated in FIG. 4 differs from that of FIG. 3 in that overall and effective reaction zone lengths are equal with only a portion of the effective length being graded from minimum reactivity nearest the feed end to maximum reactivity nearest the exit end. The first 15% of the reaction zone is an intermediate reactivity zone and, like the dead zone in FIG. 3, serves as a preheating zone.

Referring again to FIG. 2, the air and n-butane feed passes into contact with catalyst in tubes 17 and 19 under oxidation conditions whereby n-butane is oxidized to maleic anhydride and by-products. There is a pressure drop from the feed end to the exit end such that reactor effluent passes out of the exit end of the reactor to scrubber 25 via line 23.

In the scrubber, effluent is contacted counter-currently with an aqueous solution of maleic acid that is pumped to the top of the scrubber from scrubber solution tank 29 via lines 31 and 33, pump 35, line 37, cooler 39 and line 40. Maleic anhydride and by-product oxygenated hydrocarbons from the effluent are absorbed by the scrubber liquid and pass by gravity through line 27 to the scrubber solution tank. The use of an aqueous scrubber solution results in substantial hydrolysis of maleic anhydride to maleic acid. Most of the maleic acid collected in the scrubber solution tank passes to a product recovery and purification section (not shown) via line 31.

Gaseous effluent from scrubber 25, comprising inert gases, unreacted n-butane and oxygen, and any maleic anhydride and by-product oxygenated hydrocarbons not removed by the scrubber liquid, pass overhead from scrubber 25 via line 41 to condenser 43 wherein vaporized scrubber liquid passing overhead is condensed out of the effluent.

From the condenser, effluent passes to filter 53 via line 45 which also feeds to purge line 47. The purge line is equipped with back pressure valve 49, which regulates pressure in the product recovery section. The purge stream passes from the back pressure valve through line 51 to an incinerator or other disposal equipment (not shown). The remaining effluent from line 45 passes to filter 53 wherein solids, for example maleic and fumaric acids, are removed from the gas stream.

The filtered effluent then passes to compressor 57 via line 55. Compressed effluent is conveyed to recycle feed line 11 via recycle line 59.

As the process proceeds, levels of inerts supplied to the reactor in the recycle gas build up, and, when the inerts reach an appropriate proportion of the total feed to the reactor, preferably about 70 to about 95mole%, the air feed preferably is discontinued and oxygen is fed to the reactor via lines 9 and 13 in order to reduce purge stream requirements and thereby increase the amount of n-butane recycled to the reactor. In the alternative, the air feed is simply continued. It also is contemplated to use oxygen instead of air on startup.

The following examples illustrate the present invention, it being understood that the same are for purposes of illustration and not limitation.

GENERAL EXPERIMENTAL PROCEDURE (A) Molten Salt-Cooled Tubular Reaction Zone

The reaction zone used in all runs was a vertical, stainless steel tube having a length of 8 feet (2.44 meters) and an inner diameter of 1.049 inches (2.66 cm). A thermowell having an outer diameter of 0.375 inch (0.953 cm) was provided along the axis of the reaction tube. The thermowell contained a travelling thermocouple assembly consisting of eight individual thermocouples spaced at one foot intervals. During oxidation runs the reaction tube was immersed in a bath of molten salt, consisting of a eutectic mixture of sodium nitrate, sodium nitrite and potassium nitrate, contained in a stainless steel shell having a length of 8 feet (2.44 meters) and an inner diameter of 4 inches (10.2 cm). The salt bath was heated with an electric coil located at the exterior of the shell. Nitrogen was bubbled through the salt bath at a rate of about 1 SCFH to provide circulation around the reaction tube.

(B) Graded Catalyst Bed

The catalyst employed in all runs was a zinc-promoted phosphorus-vanadium-oxygen complex containing 1.19 atoms phosphorus and 0.2 atoms zinc per atom of vanadium and prepared substantially according to Example I of U.S. Pat. No. 3,862,146. The catalyst was used in the form of cylindrical pellets 3/16 inch (0.48 cm) long by 3/16 inch (0.48 cm) diameter. As loaded, catalyst bulk density was 67.4 lbs/ft$^3$ (1.08 g/cm$^3$).

Catalyst gradation was accomplished by blending weighed amounts of catalyst and alumina pellets (identified by the Norton Company trademark "Denstone") of the same shape and size as the catalyst pellets. Bulk densities of the catalyst-Denstone blends were the same as that of the pure catalyst. The reaction zone had a 1 foot (0.3 meter) feed end dead zone and a ½ foot (0.15 meter) exit end dead zone, both of which contained only Denstone pellets. Effective length was 6½ feet (1.98 meter), the entirety of which was graded from minimum reactivity nearest the feed end to maximum reactivity nearest the exit end according to the following profile:

| ZONE | LENGTH (ft.) | WEIGHT (g) CATALYST | WEIGHT (g) DENSTONE | REACTIVITY (%) |
|---|---|---|---|---|
| I | 2.6 (0.79 m) | 208 | 208 | 50 |
| II | 1.3 (0.40 m) | 131 | 77 | 63 |
| III | 1.3 (0.40 m) | 166 | 42 | 80 |
| IV | 1.3 (0.40 m) | 208 | 0 | 100 |

(C) Feed Gases

Commercial grade n-butane was used in all runs. Typical analysis, reported in mole %, was as follows:

| | |
|---|---|
| Ethane | 0–0.05% |
| Propane | 0.09–0.54% |
| i-Butane | 1.63–1.77% |
| n-Butane | 96.7–96.84% |
| Butene-1 | 0–0.038% |
| i-Butene | 0–0.028% |
| i-Pentene | 0.06–1.04% |
| t-Butene-2 | 0–0.067% |
| c-Butene-2 | 0.040–0.74% |
| C$_5$ and higher | 0–0.480% |

Oxygen, when used, was extra dry grade having a minumum purity of 99.6%. Air, when used, had a maximum moisture content of 0.3%.

(D) Operation

For all runs, DP cells with integral orifices were used to feed oxygen, air and recycle gas. n-Butane was metered to the reaction tube using a DP cell equipped with a 0.069 inch (0.18 cm) inner diameter, 90 feet (27.4 meter) long capillary, which aided in maintaining laminar flow and a suitable pressure drop. The n-butane assembly was installed in a 150° F. (66° C.) oven to ensure reproducibility of feed rates.

Prior to introduction into the reaction tube, the feed gases were mixed and heated to 350° F. (177° C.). The feed then was fed to the top of the reaction tube which was maintained at 15 psig (1.05 kg/cm$^2$). Feed composition, reaction conditions and feed rate are shown in the tables appearing hereinbelow.

Effluent exited the reaction tube at its bottom, which was under pressure of 14 psig (0.98 kg/cm$^2$), and was passed through a filter to remove entrained catalyst particles. The filtered effluent then was passed through a pressure control valve and from there to a primary scrubber consisting of a 2½ foot (0.76 m) long, 4 inch (10.2 cm) inner diameter glass pipe filled with ½ inch (1.3 cm) ceramic saddles. In the primary scrubber, the effluent was contacted counter-currently with aqueous maleic acid. Most of the maleic anhydride in the effluent was removed in the primary scrubber. Scrubbed effluent was passed from the primary scrubber to a secondary scrubber which consisted of a 2 foot (0.61 m) long, 4 inch (10.1 cm) inner diameter glass pipe filled with ⅜ inch (0.95 cm) ceramic saddles. The bottom half of the secondary scrubber was filled with water while the top half served as a disentrainment chamber. Scrubbed effluent from the primary scrubber was bubbled through the water resulting in further removal of maleic anhydride and by-product oxygenated hydrocarbons.

Scrubbed effluent was divided into purge and recycle streams by passing a portion of the effluent through a back pressure valve maintained at about 5 psig (0.35 kg/cm$^2$) and from there to a wet test meter which measured the purge stream flow rate. In recycle runs, the recycle stream was filtered, compressed to 25 psig (1.76 kg/cm$^2$) in a diaphragm compressor and returned to the reaction tube. In comparative runs operated on a once through basis, the entire scrubbed effluent was passed to the wet test meter. Space velocity through the tube was regulated by adjustment of the recycle gas flow rate.

(E) Analyses and Yield Calculations

For all runs, feed and effluent gases were analyzed using a Fisher-Hamilton Model 1200 gas chromatograph with dual columns.

Volumetric Space Velocities (abbreviated "VSV" hereinbelow) were determined by dividing volumetric feed rates at 0° C. and 1 atmosphere by reaction zone volume.

Maleic anhydride yields were determined by potentiometric amine titration of scrubber solution samples.

Maleic anhydride productivity was determined by dividing the calculated weight of recovered maleic anhydride by the product of (1) duration and (2) the combined weight of catalyst and diluent.

Selectivity to maleic anhydride was calculated by dividing maleic anhydride molar yields by the number of moles of n-butane converted and multiplying by 100%. Selectivity based on total hydrocarbon feed can be calculated by multiplying selectivities based on n-butane by 0.96.

EXAMPLE 1

A series of oxidations was conducted over the course of several days. Feed compositions, mode of operation, reaction conditions and results are shown in TABLE 1.

TABLE 1

| RUN NO. | 1 | 2 | 3 | 4 |
|---|---|---|---|---|
| MODE | OTA[1] | RA[2] | RA | RA |
| FEED (mole %) | | | | |
| n-C$_4$ | 1.46 | 2.89 | 3.00 | 3.97 |
| O$_2$ | 20.6 | 12.1 | 12.7 | 12.9 |
| CO | 0 | 2.07 | 1.90 | 1.74 |
| CO$_2$ | 0.03 | 1.58 | 1.54 | 1.43 |
| N$_2$ | 77.0 | 80.4 | 79.9 | 79.0 |
| TEMP (°F.) | | | | |
| Hot Spot | 826 | 830 | 826 | 829 |
| Salt Bath | 767 | 757 | 754 | 745 |
| VSV (hr$^{-1}$) | 1510 | 1640 | 1640 | 1630 |
| DURATION (days) | 1 | 1 | 1 | 2 |
| EFFLUENT (mole %) | | | | |
| n-C$_4$ | 0.38 | 1.53 | 1.58 | 2.47 |
| O$_2$ | 16.4 | 6.31 | 6.45 | 6.21 |
| CO | 1.27 | 3.63 | 3.55 | 3.43 |
| CO$_2$ | 0.90 | 2.76 | 2.87 | 2.82 |
| N$_2$ | 80.1 | 80.4 | 79.9 | 79.0 |
| n-C$_4$ CONVERSION (%) | | | | |
| Per Pass | — | 49.6 | 50.1 | 41.5 |
| Overall | 74.7 | 71.2 | 71.2 | 60.7 |
| MAN[3] YIELD (wt %) | 70.2 | — | 68.4 | 59.7 |
| PRODUCTIVITY[4] | 0.0390 | — | 0.0534 | 0.0597 |
| SELECTIVITY[5] | 52.7 | — | 57.0 | 58.3 |

| RUN NO. | 5 | 6 | 7 | 8 |
|---|---|---|---|---|
| MODE | RA | RA | RA | RA |
| FEED (mole %) | | | | |
| n-C$_4$ | 3.99 | 4.28 | 3.04 | 3.54 |
| O$_2$ | 12.9 | 13.0 | 11.7 | 12.1 |
| CO | 1.76 | 1.75 | 2.24 | 2.06 |
| CO$_2$ | 1.44 | 1.45 | 1.78 | 1.67 |
| N$_2$ | 79.0 | 78.6 | 80.3 | 7.97 |
| TEMP (°C.) | | | | |
| Hot Spot | 442 | 449 | 448 | 449 |
| Salt Bath | 396 | 394 | 405 | 402 |
| VSV (hr$^{-1}$) | 1630 | 1620 | 1640 | 1620 |
| DURATION (hr) | 1 | 1 | 1 | 1 |
| EFFLUENT (mole %) | | | | |
| n-C$_4$ | 2.50 | 2.69 | 1.57 | 1.98 |
| O$_2$ | 6.02 | 5.51 | 5.12 | 5.03 |
| CO | 3.49 | 3.70 | 4.03 | 3.98 |
| CO$_2$ | 2.87 | 3.04 | 3.19 | 3.20 |
| N$_2$ | 79.0 | 78.6 | 80.3 | 79.7 |
| n-C$_4$ CONVERSION (%) | | | | |
| Per Pass | 41.2 | 41.2 | 51.2 | 47.4 |
| Overall | 60.1 | 59.0 | 71.9 | 66.1 |
| MAN YIELD (wt %) | 59.5 | 58.7 | 69.3 | 62.1 |
| PRODUCTIVITY | 0.0596 | 0.0622 | 0.0542 | 0.0566 |
| SELECTIVITY | 58.7 | 59.5 | 57.1 | 55.7 |

[1] In this and all subsequent tables "OTA" stands for once through air oxidation.
[2] In this and all subsequent tables "RA" stands for recycle runs using air as the molecular oxygen source.
[3] In this and all subsequent tables "MAN" stands for maleic anhydride.
[4] In this and all subsequent tables MAN Productivity is reported in grams MAN/(gram (catalyst + diluent)) (hour).
[5] In this and all subsequent tables MAN Selectivity is reported in mole %.

EXAMPLE 2

Over four consecutive days a series of four runs was conducted. Details are reported in TABLE 2.

TABLE 2

| RUN NO. | 1 | 2 | 3 | 4 |
|---|---|---|---|---|
| MODE | OTA | OTA | RA | RA |
| FEED (mole %) | | | | |
| n-C$_4$ | 1.52 | 1.52 | 3.65 | 4.61 |
| O$_2$ | 20.7 | 20.7 | 12.0 | 12.6 |
| CO | 0 | 0 | 2.15 | 1.92 |
| CO$_2$ | 0.03 | 0.03 | 3.34 | 3.36 |
| N$_2$ | 76.9 | 76.9 | 79.6 | 78.4 |
| TEMP (°C.) | | | | |
| Hot Spot | 443 | 431 | 446 | 448 |
| Salt Bath | 409 | 402 | 399 | 395 |
| VSV (hr$^{-1}$) | 1510 | 1510 | 1620 | 1630 |

TABLE 2-continued

| RUN NO. | 1 | 2 | 3 | 4 |
|---|---|---|---|---|
| DURATION (hr) | 3 | 1 | 1 | 1 |
| EFFLUENT (mole %) | | | | |
| n-$C_4$ | 0.32 | 0.40 | 2.08 | 2.93 |
| $O_2$ | 15.9 | 16.2 | 4.72 | 4.57 |
| CO | 1.53 | 1.34 | 4.15 | 4.05 |
| $CO_2$ | 1.14 | 1.01 | 3.34 | 3.36 |
| $N_2$ | 80.2 | 80.1 | 84.7 | 84.1 |
| n-$C_4$ CONVERSION (%) | | | | |
| Per Pass | — | — | 46.4 | 40.7 |
| Overall | 78.0 | 74.6 | 65.8 | 58.2 |
| MAN Yield (wt. %) | 66.0 | 66.1 | 61.5 | 52.6 |
| Productivity | 0.0367 | 0.0367 | 0.0553 | 0.0568 |
| Selectivity | 49.0 | 52.5 | 55.4 | 53.6 |

EXAMPLE 3

A third series of once through and recycle runs using air was conducted over several days. Details are reported in TABLE 3.

TABLE 3

| RUN NO. | 1 | 2 | 3 | 4 | 5 |
|---|---|---|---|---|---|
| MODE | OTA | RA | RA | RA | OTA |
| FEED (mole %) | | | | | |
| n-$C_4$ | 1.44 | 6.12 | 5.22 | 6.14 | 1.72 |
| $O_2$ | 16.4 | 12.1 | 15.9 | 13.3 | 16.1 |
| CO | 0 | 1.93 | 1.02 | 1.62 | 0 |
| $CO_2$ | 0.03 | 1.72 | 0.86 | 1.43 | 0.03 |
| $N_2$ | 76.9 | 77.2 | 76.1 | 76.7 | 76.7 |
| TEMP (°C.) | | | | | |
| Hot Spot | 433 | 452 | 455 | 447 | 430 |
| Salt Bath | 404 | 391 | 383 | 385 | 398 |
| VSV ($hr^{-1}$) | 1510 | 1490 | 1530 | 1551 | 1510 |
| DURATION (hr) | 3 | 1 | 1 | 1 | 3 |
| EFFLUENT (mole %) | | | | | |
| n-$C_4$ | 0.35 | 4.33 | 3.28 | 4.27 | 0.42 |
| $O_2$ | 16.4 | 2.69 | 6.64 | 3.66 | 15.4 |
| CO | 1.34 | 4.47 | 3.52 | 4.17 | 1.58 |
| $CO_2$ | 1.01 | 3.94 | 2.96 | 3.66 | 1.24 |
| $N_2$ | 80.0 | 83.6 | 82.7 | 83.3 | 80.4 |
| n-$C_4$ CONVERSION (%) | | | | | |
| Per Pass | — | 34.6 | 42.1 | 35.9 | — |
| Overall | 76.5 | 49.7 | 51.5 | 49.3 | 76.0 |
| MAN Yield (wt. %) | 67.4 | 43.3 | 46.5 | 43.7 | 67.0 |
| Productivity | 0.0373 | 0.0540 | 0.0580 | 0.0529 | 0.0371 |
| Selectivity | 52.2 | 51.6 | 53.5 | 52.6 | 51.8 |

Comparison of the once through-air (OTA) and recycle-air (RA) runs in EXAMPLES 1-3 and TABLES 1-3 shows that productivity in the latter was substantially greater than in the once through mode although in other respects, results were generally comparable.

Due to incomplete activation of the catalyst in EXAMPLES 1-3, reaction rates were low and several brief temperature runaways occurred. Runaways were easily controlled by minor reductions in n-butane feed rates and salt bath temperature. After the catalyst was sufficiently activated (Example 3 Run 4) no more runaways occurred.

EXAMPLE 4

In this example a series of recycle runs with oxygen was followed by a once through, air oxidation run. Details are reported in TABLE 4.

TABLE 4

| RUN NO. | 1 | 2 | 3 | 4 | 5 |
|---|---|---|---|---|---|
| MODE | RO[(1)] | RO | RO | RO | RO |
| FEED (mole %) | | | | | |
| n-$C_4$ | 3.17 | 3.04 | 3.44 | 3.84 | 4.83 |
| $O_2$ | 11.8 | 15.6 | 15.3 | 15.5 | 13.6 |
| CO | 43.9 | 41.7 | 42.0 | 42.2 | 42.8 |
| $CO_2$ | 40.4 | 39.0 | 38.5 | 37.7 | 38.2 |
| $N_2$ | 0.68 | 0.62 | 0.80 | 0.68 | 0.55 |
| TEMP (°C.) | | | | | |
| Hot Spot | 442 | 445 | 444 | 443 | 450 |
| Salt Bath | 406 | 403 | 401 | 398 | 185 397 |
| VSV ($hr^{-1}$) | 1590 | 1550 | 1600 | 1610 | 1570 |
| DURATION (days) | 1 | 1 | 2 | 1 | 1 |
| EFFLUENT (mole %) | | | | | |
| n-$C_4$ | 1.75 | 1.45 | 1.84 | 2.17 | 3.10 |
| $O_2$ | 5.28 | 8.34 | 7.64 | 7.61 | 5.03 |
| CO | 47.9 | 46.2 | 46.8 | 47.1 | 48.0 |
| $CO_2$ | 44.4 | 43.4 | 43.2 | 42.6 | 43.3 |
| $N_2$ | 0.71 | 0.58 | 0.58 | 0.52 | 0.59 |
| n-$C_4$ CONVERSION (%) | | | | | |
| Per Pass | 48.0 | 55.1 | 49.9 | 47.3 | 40.3 |
| Overall | 96.7 | 96.6 | 95.6 | 95.3 | 93.8 |
| MAN Yield (wt. %) | 86.4 | 86.1 | 84.2 | 84.5 | 77.1 |
| Productivity | 0.0525 | 0.0566 | 0.0595 | 0.0637 | 0.0615 |
| Selectivity | 53.0 | 52.8 | 52.2 | 52.6 | 48.7 |

| RUN NO. | 6 | 7 | 8 | 9 |
|---|---|---|---|---|
| MODE | RO | RO | RO | RO |
| FEED (mole %) | | | | |
| n-$C_4$ | 4.90 | 3.65 | 4.00 | 1.48 |
| $O_2$ | 16.5 | 15.3 | 15.9 | 20.7 |
| CO | 41.5 | 42.9 | 42.4 | 0 |
| $CO_2$ | 36.6 | 37.6 | 37.2 | 0.03 |
| $N_2$ | 0.54 | 0.59 | 0.55 | 76.9 |
| TEMP (°C.) | | | | |
| Hot Spot | 449 | 448 | 447 | 432 |
| Salt Bath | 392 | 403 | 401 | 403 |
| VSV ($hr^{-1}$) | 1530 | 1910 | 1960 | 1510 |
| DURATION (days) | 3 | 1 | 1 | 1 |
| EFFLUENT (mole %) | | | | |
| n-$C_4$ | 3.04 | 2.06 | 2.42 | 0.35 |
| $O_2$ | 7.50 | 8.02 | 8.34 | 16.1 |
| CO | 47.0 | 47.4 | 47.0 | 0.35 |
| $CO_2$ | 42.0 | 42.0 | 41.7 | 1.16 |
| $N_2$ | 0.42 | 0.50 | 0.54 | 80.0 |
| n-$C_4$ CONVERSION (%) | | | | |
| Per Pass | 42.8 | 47.1 | 43.5 | — |
| Overall | 93.7 | 95.8 | 94.6 | 77.2 |
| MAN Yield (wt. %) | 75.5 | 79.3 | 82.2 | 61.2 |
| Productivity | 0.0634 | 0.0668 | 0.0725 | 0.0340 |
| Selectivity | 47.7 | 49.1 | 51.5 | 47.0 |

[(1)] In this and all subsequent tables, "RO" stands for recycle runs using 96% pure oxygen.

EXAMPLE 5

Subsequent to the runs in EXAMPLE 4 the oxidation catalyst was regenerated by passing 9 ml carbon tetrachloride over the catalyst at 404° C. in 0.077 SCFM nitrogen over a period of 15 minutes. The carbon tetrachloride and nitrogen were introduced into the exit end of the reaction tube.

Following regeneration four recycle runs were carried out using oxygen. Details are reported in TABLE 5.

TABLE 5

| RUN NO. | 1 | 2 | 3 | 4 |
|---|---|---|---|---|
| MODE | RO | RO | RO | RO |
| FEED (mole %) | | | | |
| n-C$_4$ | 3.24 | 4.06 | 4.12 | 4.76 |
| O$_2$ | 12.2 | 12.6 | 15.4 | 15.2 |
| CO | 46.0 | 45.3 | 43.6 | 43.6 |
| CO$_2$ | 38.1 | 37.4 | 36.1 | 35.9 |
| N$_2$ | 0.52 | 0.62 | 0.86 | 0.54 |
| TEMP (°C.) | | | | |
| Hot Spot | 449 | 449 | 449 | 450 |
| Salt Bath | 412 | 407 | 403 | 400 |
| VSV (hr$^{-1}$) | 1750 | 1830 | 1950 | 2010 |
| DURATION (days) | 3 | 1 | 1 | 1 |
| EFFLUENT (mole %) | | | | |
| n-C$_4$ | 1.75 | 2.53 | 2.53 | 3.15 |
| O$_2$ | 5.40 | 5.36 | 7.80 | 7.35 |
| CO | 49.9 | 49.7 | 48.2 | 48.4 |
| CO$_2$ | 42.4 | 41.8 | 40.8 | 40.5 |
| N$_2$ | 0.57 | 0.66 | 0.76 | 0.57 |
| n-C$_4$ CONVERSION (%) | | | | |
| Per Pass | 49.3 | 41.8 | 42.7 | 38.3 |
| Overall | 97.1 | 95.5 | 94.7 | 93.6 |
| MAN | | | | |
| Yield (wt. %) | 91.4 | 90.3 | 90.1 | 88.3 |
| Productivity | 0.0646 | 0.0721 | 0.0794 | 0.0849 |
| Selectivity | 55.8 | 56.0 | 56.4 | 56.0 |

EXAMPLE 5 and TABLE 5 illustrate a preferred manner of operating according to this invention. As can be seen, ultimate conversions of n-butane ranging from about 94 to 97% were attained at sufficiently high selectivities that maleic anhydride yields of about 90% were achieved. Productivity in Runs 3 and 4 was about double that of the once through air oxidation runs in previous examples.

EXAMPLE 6

Another series of recycle runs with oxygen was conducted over five consecutive days and then a once through air oxidation was carried out. Details are reported in TABLE 6.

TABLE 6

| RUN NO. | 1 | 2 | 3 | 4 | 5 | 6 |
|---|---|---|---|---|---|---|
| MODE | RO | RO | RO | RO | RO | OTA |
| FEED (mole %) | | | | | | |
| n-C$_4$ | 5.24 | 5.36 | 5.18 | 4.83 | 4.73 | 1.52 |
| O$_2$ | 14.2 | 14.4 | 14.2 | 15.2 | 15.7 | 20.7 |
| CO | 43.4 | 43.2 | 43.4 | 43.1 | 42.6 | 0 |
| CO$_2$ | 36.5 | 36.6 | 36.6 | 36.3 | 36.4 | 0.03 |
| N$_2$ | 0.57 | 0.48 | 0.52 | 0.54 | 0.54 | 76.9 |
| TEMP (°C.) | | | | | | |
| Hot Spot | 448 | 447 | 449 | 454 | 451 | 433 |
| Salt Bath | 398 | 398 | 399 | 398 | 399 | 405 |
| VSV (hr$^{-1}$) | 2030 | 1980 | 1950 | 1970 | 1980 | 1510 |
| DURATION (days) | 4 | 1 | 1 | 1 | 1 | 3 |
| EFFLUENT (mole %) | | | | | | |
| n-C$_4$ | 3.69 | 3.78 | 3.56 | 3.19 | 3.08 | 0.37 |
| O$_2$ | 6.42 | 6.55 | 6.35 | 7.35 | 7.72 | 16.0 |
| CO | 48.1 | 48.0 | 48.3 | 47.8 | 47.5 | 1.52 |
| CO$_2$ | 41.1 | 41.1 | 41.3 | 41.1 | 41.1 | 1.16 |
| N$_2$ | 0.68 | 0.51 | 0.49 | 0.54 | 0.60 | 80.0 |
| n-C$_4$ CONVERSION (%) | | | | | | |
| Per Pass | 34.0 | 34.2 | 36.3 | 38.7 | 39.1 | |
| Overall | 92.3 | 92.8 | 93.7 | 94.1 | 93.4 | 76.6 |
| MAN | | | | | | |
| Yield (wt. %) | 82.5 | 82.5 | 82.5 | 82.5 | 82.3 | 63.0 |
| Productivity | 0.0794 | 0.0794 | 0.0794 | 0.0794 | 0.0792 | 0.0350 |
| Selectivity | 53.0 | 52.0 | 52.0 | 52.0 | 52.2 | 48.7 |

EXAMPLE 7

Following regeneration of catalyst according to the procedure of EXAMPLE 5 a once through air oxidation was conducted and then five recycle runs with oxygen were carried out over five consecutive days. Details are reported in TABLE 7.

From the table it can be seen that selectivity varies somewhat depending on n-butane concentration. For the catalyst used in these examples, selectivity was best when n-butane concentration was about 5 mole %.

TABLE 7

| RUN NO. | 1 | 2 | 3 | 4 | 5 | 6 |
|---|---|---|---|---|---|---|
| MODE | OTA | RO | RO | RO | RO | RO |
| FEED (mole %) | | | | | | |
| n-C$_4$ | 1.49 | 7.28 | 6.12 | 5.88 | 5.72 | 5.10 |
| O$_2$ | 20.8 | 11.8 | 13.5 | 14.6 | 14.0 | 14.8 |
| CO | 0 | 42.3 | 42.6 | 42.0 | 42.3 | 42.5 |
| CO$_2$ | 0.03 | 38.0 | 37.0 | 37.0 | 37.3 | 36.8 |
| N$_2$ | 76.8 | 0.61 | 0.69 | 0.48 | 0.64 | 0.69 |
| TEMP (°C.) | | | | | | |
| Hot Spot | 430 | 451 | 451 | 452 | 448 | 447 |
| Salt Bath | 406 | 399 | 398 | 396 | 397 | 398 |
| VSV (hr$^{-1}$) | 1510 | 1760 | 1740 | 1740 | 1840 | 1880 |
| DURATION (days) | 1 | 3 | 1 | 1 | 1 | 1 |

TABLE 7-continued

| RUN NO. | 1 | 2 | 3 | 4 | 5 | 6 |
|---|---|---|---|---|---|---|
| EFFLUENT (mole %) | | | | | | |
| n-$C_4$ | 0.37 | 5.71 | 4.40 | 4.11 | 4.04 | 3.48 |
| $O_2$ | 16.4 | 2.89 | 4.54 | 5.67 | 5.66 | 6.82 |
| CO | 1.31 | 47.3 | 48.1 | 47.4 | 47.5 | 47.5 |
| $CO_2$ | 1.01 | 43.4 | 42.3 | 42.1 | 42.2 | 41.5 |
| $N_2$ | 80.0 | 0.62 | 0.68 | 0.68 | 0.61 | 0.72 |
| n-$C_4$ CONVERSION (%) | | | | | | |
| Per Pass | | 27.4 | 33.6 | 35.4 | 34.6 | 36.3 |
| Overall | 76.2 | 89.4 | 91.6 | 92.1 | 92.6 | 92.7 |
| MAN | | | | | | |
| Yield (wt. %) | 73.3 | 70.6 | 81.5 | 83.3 | 82.8 | 85.9 |
| Productivity | 0.0408 | 0.0679 | 0.0784 | 0.0805 | 0.0796 | 0.0826 |
| Selectivity | 57.0 | 46.8 | 52.8 | 53.6 | 53.0 | 54.9 |

EXAMPLE 8

Another series of recycle runs with oxygen was followed by a once through run with air. Details are reported in TABLE 8.

TABLE 8

| RUN NO. | 1 | 2 | 3 | 4 | 5 |
|---|---|---|---|---|---|
| MODE | RO | RO | RO | RO | OTA |
| FEED (mole %) | | | | | |
| n-$C_4$ | 5.66 | 5.53 | 5.24 | 5.34 | 1.46 |
| $O_2$ | 13.4 | 13.7 | 14.3 | 14.2 | 20.8 |
| CO | 42.8 | 42.5 | 42.5 | 42.2 | 0 |
| $CO_2$ | 37.5 | 37.6 | 37.3 | 37.7 | 0.03 |
| $N_2$ | 0.61 | 0.64 | 0.77 | 0.59 | 76.8 |
| TEMP (°C.) | | | | | |
| Hot Spot | 449 | 448 | 440 | 438 | 433 |
| Salt Bath | 398 | 398 | 397 | 395 | 406 |
| VSV ($hr^{-1}$) | 1940 | 1950 | 2110 | 2160 | 1510 |
| DURATION (days) | 3 | 3 | 1 | 3 | 1 |
| EFFLUENT (mole %) | | | | | |
| n-$C_4$ | 4.07 | 3.93 | 3.74 | 3.90 | 0.34 |
| $O_2$ | 5.12 | 5.46 | 6.72 | 6.57 | 15.9 |
| CO | 48.1 | 47.8 | 47.1 | 46.8 | 0.34 |
| $CO_2$ | 42.1 | 42.1 | 41.5 | 42.1 | 1.25 |
| $N_2$ | 0.67 | 0.70 | 0.87 | 0.60 | 80.0 |
| n-$C_4$ CONVERSION (%) | | | | | |
| Per Pass | 32.8 | 33.4 | 32.9 | 31.1 | |
| Overall | 91.0 | 90.9 | 91.8 | 90.4 | 77.6 |
| MAN Yield (wt. %) | 81.7 | 80.1 | 84.6 | 80.6 | 62.4 |
| Productivity | 0.0792 | 0.0777 | 0.0819 | 0.0781 | 0.0347 |
| Selectivity | 53.2 | 52.2 | 54.6 | 52.9 | 47.6 |

From the foregoing examples and tables, it can be appreciated that operation in accordance with the present invention can result in substantial improvements over typical once through air operations. Among these improvements are increases in reactor productivity by more than 100% in some cases and reduction in butane consumption per unit weight of product.

We claim:

1. A process for producing maleic anhydride comprising (A) contacting a non-flammable feed consisting essentially of about 3 to about 8 mole % n-butane, 8 to about 20 mole % molecular oxygen, and a balance of at least one inert gas with at least one n-butane oxidation catalyst in a heat transfer medium-cooled, tubular reaction zone maintained under oxidation conditions effective to yield a relatively low per pass conversion of n-butane, said catalyst being graded along at least a portion of the effective length of the reaction zone so as to provide minimum reactivity nearest the feed end of the reaction zone and maximum reactivity nearest the exit end of the reaction zone, with staged or continuous increase in reactivity between the areas of minimum and maximum reactivity;

(B) withdrawing from the reaction zone an effluent comprising maleic anhydride, by-product oxygenated hydrocarbons, carbon oxides, n-butane and oxygen;

(C) separating a major portion of maleic anhydride and oxygenated hydrocarbon by-products from said effluent;

(D) removing from the effluent remaining after recovery of maleic anhydride and oxygenated hydrocarbon by-products a purge stream at a rate substantially corresponding to the rate of build-up of inert gases in the reaction zone; and (E) recycling effluent remaining after removal of the purge stream to the reaction zone with addition of make-up gases comprising n-butane and oxygen.

2. The process of claim 1 wherein the molecular oxygen is substantially pure and the inert gas consists essentially of a mixture of carbon monoxide and carbon dioxide.

3. The process of claim 2 wherein only a portion of the effective reaction zone length is graded from minimum reactivity nearest the feed end to maximum reactivity nearest the exit end, the remainder of the effective length being located at the feed end and serving as a preheating zone for the feed.

4. The process of claim 2 wherein the entire effective length of the reaction zone is graded from minimum reactivity nearest the feed end to maximum reactivity nearest the exit end.

5. The process of claim 4 wherein the feed consists essentially of about 3 to about 8 mole % n-butane, about 8 to about 18 mole % molecular oxygen, about 30 to about 50 mole % carbon monoxide, about 35 to about 55 mole % carbon dioxide and less than about 1 mole % nitrogen.

6. The process of claim 5 wherein the minimum reactivity zone nearest the feed end extends over about 10 to about 50% of the effective reaction zone length and reactivity in said zone ranges from about 10 to about 75% of that in the maximum reactivity zone nearest the exit end.

7. The process of claim 1 wherein the source of oxygen is air and the inert gas contained in the feed consists essentially of nitrogen.

8. The process of claim 7 wherein only a portion of the effective reaction zone length is graded from minimum reactivity nearest the feed end to maximum reactivity nearest the exit end, the remainder of the effective length being located at the feed end and serving as a preheating zone for the feed.

9. The process of claim 7 wherein the entire effective length of the reaction zone is graded from minimum reactivity nearest the feed end to maximum reactivity nearest the exit end.

10. The process of claim 9 wherein the feed consists essentially of about 3 to about 8 mole % n-butane, about 10 to about 18 mole % molecular oxygen, about 1 to about 10 mole % carbon monoxide, up to about 5 mole % carbon dioxide and about 70 to about 85 mole % nitrogen.

11. The process of claim 10 wherein the minimum reactivity zone nearest the feed end extends over about 10 to about 50% of the effective reaction zone length and reactivity in said zone ranges from about 10 to about 75% of that in the maximum reactivity zone nearest the exit end.

12. The process of claim 1 wherein the oxidation catalyst comprises a phosphorus-vanadium-oxygen complex.

13. The process of claim 1 wherein the oxidation catalyst is a metal-activated phosphorus-vanadium-oxygen complex.

14. A process for producing maleic anhydride comprising:
(A) contacting a non-flammable feed consisting essentially of about 3 to about 8 mole % n-butane, about 8 to about 18 mole % molecular oxygen and a balance of inert gas comprising carbon monoxide, carbon dioxide, nitrogen or mixtures thereof with at least one n-butane oxidation catalyst in a molten salt-cooled, tubular reaction zone at about 350° to about 500° C., about 10 to about 70 psi and at a volumetric space velocity of about 1500 to about 2500 hr$^{-1}$, whereby a per pass n-butane conversion of about 30 to about 50% is attained, said catalyst being graded along the effective reaction zone length such that a minimum reactivity zone nearest the feed end of the reaction zone occupies about 10 to about 50% of effective reaction zone length and contains catalyst of about 10 to about 75% relative reactivity, with the remainder of the effective length being divided into about 2 to about 7 reactivity zones of approximately equal length and increasing reactivity;
(B) withdrawing from the exit end of the reaction zone an effluent comprising maleic anhydride, by-product oxygenated hydrocarbons, carbon oxides, n-butane and oxygen;
(C) separating a major portion of maleic anhydride and oxygenated hydrocarbon by-products from said effluent;
(D) removing from the effluent remaining after recovery of maleic anhydride and oxygenated hydrocarbon by-products a purge stream at a rate substantially corresponding to the rate of build-up of inert gases in the reaction zone; and
(E) recycling effluent remaining after removal of the purge stream to the reaction zone with addition of make-up gases comprising n-butane and oxygen.

15. The process of claim 14 wherein the molecular oxygen source is substantially pure molecular oxygen and the ballast gas is a mixture of carbon monoxide and carbon dioxide.

16. The process of claim 14 wherein the molecular oxygen source is air and the inert gas comprises a major amount of nitrogen and minor amounts of carbon oxides.

17. The process of claim 14 wherein the oxidation catalyst comprises a phosphorus-vanadium-oxygen complex.

18. The process of claim 14 wherein the oxidation catalyst is a metal promoted phosphorus-vanadium-oxygen complex.

19. The process of any of claims 1–18 wherein grading of catalyst in terms of reactivity is accomplished by blending of catalyst with inerts.

20. The process of any of claims 1–18 wherein grading of catalyst in terms of reactivity is accomplished by partial impregnation of catalyst support.

21. The process of any of claims 1–18 wherein grading of catalyst in terms of reactivity is accomplished through the use of catalysts of varying reactivities.

22. The process of any of claims 1–18 wherein grading of the catalyst in terms of reactivity is accomplished by blending catalysts of varying reactivities.

* * * * *

UNITED STATES PATENT OFFICE
CERTIFICATE OF CORRECTION

Patent No. 4,342,699    Dated August 3, 1982

Inventor(s) David A. Palmer, Juergen K. Holzhauer

It is certified that error appears in the above-identified patent and that said Letters Patent are hereby corrected as shown below:

| Column | Line | Reads | Should Read |
|---|---|---|---|
| 3 | 41 | ", pp 93-106" | --, pp. 93-106-- |
| 3 | 47 | ", pp 38-43" | --, pp. 38-43-- |
| 7 | 17 | "serparate" | --separate-- |
| 8 | 62 | "1,403,395" | --"British 1,403,395-- |
| 9 | 1&2 | "titanium beryllium" | --titanium, beryllium-- |
| 9 | 9 | "chromium cobalt" | --chromium, cobalt-- |
| 14 | 41 | "(C) Feed Gases" | -- there is no footnote to table-- |
| 15 | 20 | "(10.1cm)" | --(10.2cm)-- |

UNITED STATES PATENT OFFICE
CERTIFICATE OF CORRECTION

Patent No. 4,342,699      Dated August 3, 1982

Inventor(s) David A. Palmer, Juergen K. Holzhauer

It is certified that error appears in the above-identified patent and that said Letters Patent are hereby corrected as shown below:

| Column | Line | Reads | Should Read |
|---|---|---|---|
| 18 | 18 | "401 398 185 397" | --401 398 397-- |
| 18 | 40 | "RO RO RO RO" | --RO RO RO OTA-- |
| 20 | 25 | "43.4 43.2 43.4" | --43.5 43.2 43.4-- |

Signed and Sealed this

Twenty-fourth Day of January 1984

[SEAL]

Attest:

Attesting Officer

GERALD J. MOSSINGHOFF

Commissioner of Patents and Trademarks